United States Patent [19]

Herskovitz et al.

[11] Patent Number: 4,482,635
[45] Date of Patent: Nov. 13, 1984

[54] COMPOSITION, INDICATOR, PROCESS AND DEVICE FOR DETECTING CARBON MONOXIDE

[75] Inventors: Thomas Herskovitz, Wilmington; William G. Peet, Newark, both of Del.

[73] Assignee: E. I. Du Pont de Nemours & Company, Wilmington, Del.

[21] Appl. No.: 534,779

[22] Filed: Sep. 22, 1983

Related U.S. Application Data

[63] Continuation of Ser. No. 363,283, Mar. 29, 1982, abandoned, which is a continuation-in-part of Ser. No. 236,245, Feb. 20, 1981, abandoned.

[51] Int. Cl.$^3$ .......................... G01N 21/25; G01J 1/50
[52] U.S. Cl. ........................................ 436/134; 422/86; 422/87; 436/167; 436/178; 436/902; 502/217
[58] Field of Search .................... 252/408, 458, 459; 436/134, 167, 175, 178, 902; 502/200, 217; 422/86, 87

[56] References Cited

U.S. PATENT DOCUMENTS

| 2,487,077 | 11/1949 | Shepherd | 436/134 |
| 3,245,917 | 4/1966 | Mayo, Jr. | 436/134 |
| 3,507,623 | 4/1970 | McConnaughey | 422/86 |
| 3,884,641 | 5/1975 | Kraffczyk et al. | 422/87 X |
| 4,043,934 | 8/1977 | Shuler et al. | 436/134 |
| 4,096,227 | 6/1978 | Gore | 264/210.6 X |
| 4,208,194 | 6/1980 | Nelson | 55/158 |
| 4,225,464 | 9/1980 | Scholten et al. | 252/458 |
| 4,280,929 | 7/1981 | Shaw et al. | 252/458 X |
| 4,289,709 | 9/1981 | Kaiser | 252/458 X |

FOREIGN PATENT DOCUMENTS 477288 9/1951 Canada .

OTHER PUBLICATIONS

Analytical Chemistry, vol. 19, No. 2; Feb. 1947; pp. 77–81; Shepherd.

Primary Examiner—Kenneth M. Schor
Attorney, Agent, or Firm—Frederick D. Hunter

[57] ABSTRACT

There are disclosed an improved CO indicating composition consisting essentially of fumed silica having dispersed thereon dry residues of impregnation with a solution of palladium sulfate, sulfuric acid and ammonium molybdate, a CO indicator comprising a strip of a composite of expanded, amorphous-locked tetrafluoroethylene polymer and fumed silica having dried residues of impregnation with the aforesaid solution, an improved detector containing said indicating composition or said indicator, and improved process for detecting CO comprising exposing pre-dried air to the indicating composition or said indicator to effect a color change, extracting colored material with distilled water or an aqueous buffer solution, and measuring the depth of color in the resulting extract.

9 Claims, 3 Drawing Figures

COMPOSITION, INDICATOR, PROCESS AND DEVICE FOR DETECTING CARBON MONOXIDE

CROSS-REFERENCE TO RELATED APPLICATION

This application is a continuation of U.S. application Ser. No. 363,283, filed on Mar. 29, 1982 and now abandoned, which in turn is a continuation-in-part of U.S. application Ser. No. 236,245 filed on Feb. 20, 1981 and now abandoned.

BACKGROUND OF THE INVENTION

This invention relates to an indicating composition, indicator strip, process and device for measuring carbon monoxide in the surrounding atmosphere. More specifically, the invention relates to an indicating composition, indicator strip, process and device whereby carbon monoxide can be measured quantitatively.

U.S. Pat. No. 2,487,077, issued to Shepherd on Nov. 8, 1949, discloses a CO indicating composition, process and detection device. The composition consists essentially of a body of purified silica gel freed of substances oxidizable by hot concentrated nitric acid and having combined therein essentially dry residues of impregnation with a solution of palladium sulfate, sulfuric acid and ammonium molybdate, in proportions by weight of about 500 to 1600 parts gel, 5 to 50 parts acid containing about 1 part palladium, and about 10 to 60 parts molybdate. The composition is free of chloride ion.

Canadian Pat. No. 477,288 discloses a granular reagent adapted to undergo a color change in the presence of carbon monoxide consisting of a partly dehydrated granular product prepared by impregnating silica gel with a salt selected from the group consisting of alkali molybdates and tungstates, with a mineral acid, and with palladous halide.

U.S. Pat. No. 3,245,917, issued to Mayo, Jr. on Apr. 12, 1966, discloses a self-regenerating reagent for detecting the presence of carbon monoxide at a relative humidity of at least 20%, consisting essentially of a carrier of silica gel having adsorbed thereon palladium chloride and a regenerating amount of hydrochloric acid.

U.S. Pat. No. 4,043,934, issued to Shuler et al on Aug. 23, 1977, discloses a self-regenerating reagent which, on contact with a reducing gas, oxidizes the gas and is reduced from an oxidized state to a reduced state. The reagent comprises a mixture of a palladium salt, a compound which includes a complex ion of a metal selected from the group consisting of molybdenum, tungsten and vanadium, and a salt of a metal selected from the group consisting of copper, nickel and iron, and a hydrophilic carrier for the mixture. Silica gel is among the possible carriers disclosed and CO detection is one of the uses disclosed for the composition.

U.S. Pat. No. 3,507,623 discloses an article for detecting CO, said article containing an indicating composition such as that disclosed in the Shepherd patent.

U.S. Pat. No. 4,096,227, issued to Gore on June 20, 1978, discloses a process for producing a porous article of a tetrafluoroethylene polymer comprising mixing polymer resin with a lubricant to form a paste, extruding the paste to form an extrudate, removing the lubricant, stretching the extrudate at a high rate (exceeding 10% per second) while maintaining the extrudate at a temperature of about 35° C. to 327° C., then heating the extrudate in a stretched condition to at least 327° C., and cooling the resultant product. The resin can contain a filler, such as asbestos or silica.

Prior art processes and devices for determining the presence of carbon monoxide in the surrounding atmosphere generally rely upon a subjective determination of CO content by comparison of the color of the exposed composition with those of standards. Moreover, for prior art compositions which use silica gel, to insure the removal of interfering impurities, the silica gel must be purified by a time-consuming process involving washing with hot nitric acid and filtration. In addition, prior art devices generally do not measure cumulative exposure to CO and are sensitive to presence of other reducing gases. There is a strong need for a CO indicating composition and/or indicator strip, process and device which readily permit quantitative and cumulative determination of the CO content of the surrounding atmosphere and which are not significantly sensitive to the presence of other reducing gases.

SUMMARY OF THE INVENTION

The present invention provides an improved CO indicating composition consisting essentially of fumed silica having dispersed thereon dry residues of impregnation with a solution of palladium sulfate, sulfuric acid and ammonium molybdate, said composition having a gram-atom ratio of Mo/Pd of from about 0.1:1 to about 350:1 and a ratio of moles of $SiO_2$/gram atoms of Pd from about 10:1 to about 5000:1. There is also provided a CO indicator comprising a strip of a composite consisting essentially of expanded, amorphous-locked tetrafluoroethylene polymer and fumed silica, such composite being from about 50% to about 95% by weight fumed silica and having dispersed thereon and therein dry residues of impregnation with the aforesaid solution. The invention further provides an improved process for detecting CO comprising exposing pre-dried ambient air to the foregoing indicating composition or indicator to effect a color change, extracting colored material with distilled water or an aqueous buffer solution, and measuring the depth of color of the resulting extract. Additionally, the invention provides an improved CO detector comprising a chamber containing said indicating composition or indicator.

DETAILED DESCRIPTION OF THE INVENTION

Figure 1:
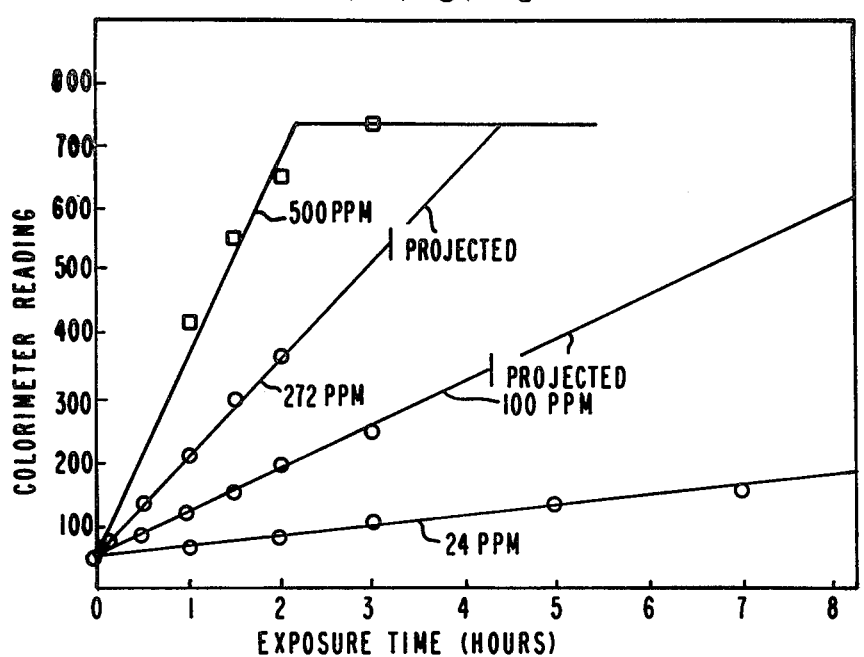
FIGS. 1–3 are graphs illustrating the linear relationship between depth of color and time of exposure obtained with the composition and indicator strip of the invention.

The composition of the invention consists essentially of fumed silica having dispersed thereon dry residues of impregnation with a solution of palladium sulfate, sulfuric acid and ammonium molybdate. In prior art formulations the silica gel used required extensive acid washing to remove organic impurities which would render the CO indicating composition useless. It has been discovered that fumed silica readily fulfills the organic-free requirement without further purification. The expression "fumed silica" as used herein means the form of silica which is produced in a high-temperature, vapor-phase process involving hydrolysis of a volatile silicon compound in a flame of hydrogen and oxygen. Usually, the silicon compound is silicon tetrachloride and a temperature typically of about 1800° C. is employed. Silica gels are prepared by wet methods, usually precipitation, at ambient or slightly elevated temperatures. Fumed silica is present in the composition of the invention in a ratio of moles of $SiO_2$/gram atoms of Pd of from about 10:1 to about 5000:1 and preferably from about 100:1 to about 1000:1. The fumed silica preferably has a surface area of at least about 100 $m^2$/g, preferably at least about 300 $m^2$/g.

In the composition of the invention dry residues of palladium sulfate and ammonium molybdate are present in a gram-atom ratio of Mo/Pd of from about 0.1:1 to about 350:1, preferably from about 1:1 to about 100:1. The starting materials for the composition of the invention are commercially available. Palladium sulfate per se can be used or palladium metal or palladium oxide can be digested with sulfuric acid to provide the solution of palladium sulfate. Similarly, either ammonium molybdate or an ammoniacal solution of potassium or sodium molybdate can be used. Preferably, palladium sulfate and ammonium molybdate are used as starting materials.

The composition of the invention can be prepared by first mixing an aqueous solution of palladium sulfate and sulfuric acid with an aqueous solution of ammonium molybdate. The two solutions can be mixed at a temperature of from about 0°–100° C. and preferably from about 20°–70° C.

After the solutions are mixed the resulting solution is filtered and the filtrate, i.e., indicator solution, obtained therefrom is added to a slurry of fumed silica. Water is removed by subjecting the resulting mixture to a vacuum at a temperature of from about 20° to 100° C., preferably from about 80° to 100° C., to provide a chrome yellow powder which is the product of the invention. If glass apparatus is used to prepare the composition of the invention, all traces of organic contamination in the apparatus have to be removed before the preparation is commenced. This removal can be effected by cleaning the apparatus with concentrated sulfuric acid. During storage and use, moisture must be kept away from the indicating composition because moisture reduces the reactivity of the indicating composition. Storage can be in a dry box or in an environment adequately protected by a desiccant, such as silica gel, calcium sulfate or potassium hydroxide.

Another aspect of the present invention is a CO indicator comprising a strip of a composite consisting essentially of expanded, amorphous-locked tetrafluoroethylene polymer and fumed silica, said composite (1) containing from about 50 to about 95% by weight of fumed silica and from about 5 to about 50% of tetrafluoroethylene polymer which has less than 0.2% by combined weight of one or more comonomers and (2) having dispersed thereon and therein dry residues of impregnation with a solution of palladium sulfate, sulfuric acid and ammonium molybdate;

Mo, Pd and $SiO_2$ being present such that Mo/Pd gram-atom ratio is from about 0.1:1 to about 350:1 and ratio of moles $SiO_2$/gram atoms of Pd is from about 10:1 to about 5000:1. Preferred values for these ratios are the same as those set forth for the composition of the invention. The weight percentages for fumed silica and tetrafluoroethylene given herein for the composite are those present in the composite prior to impregnation with the indicator solution. Preferably, the composite contains from 75 to about 95% by weight of fumed silica. The strip can have a thickness of from about 0.5 to about 6.4 mm, preferably from 0.5 to 3.0 mm.

The composite of expanded, amorphous-locked tetrafluoroethylene polymer and fumed silica can be made by the process described in U.S. Pat. No. 4,096,227 the disclosure of which is incorporated herein by reference. The process comprises blending a powder of highly crystalline tetrafluoroethylene polymer having less than 0.2% of comonomer(s) with silica, extruding the blend using a conventional lubricated extrusion technique to form an extrudate; removing the lubricant from the extrudate by conventional methods, stretching the extrudate containing unsintered polymer and silica at a rate exceeding about 10% per second while said extrudate is held at a temperature of about 35° C. to 327° C., and heating the resulting porous, stretched, silica-filled article to a temperature above the crystalline melting point of the polymer.

If the lubricant used in making the composite is an organic liquid, contains an organic liquid, or otherwise introduces organic impurities in the composite, strips of the composite must be first acid washed to provide a material free of organic impurities. The strips are then soaked in an indicator solution prepared as previously described herein to obtain impregnated strips which are dried in a manner similar to that used for the composition of the invention to provide yellow indicator strips of the invention. Storage conditions are as previously set forth herein for the composition of the invention.

The composition or indicator strip of the invention can be used to detect CO in the surrounding atmosphere at a concentration as low as about 1 ppm and at a cumulative exposure as high as about 1300 ppm-hr. In detecting or monitoring CO, a column, bed or body of the composition of the invention or an indicator strip of the invention is exposed to pre-dried air whereby a color change occurs which is proportional to the cumulative CO exposure, i.e., the product of the CO concentration, the exposure time and, if applicable, the CO flow rate. The exposure of the composition or strip to the ambient atmosphere can be effected by passing pre-dried air over the composition or strip or by providing an inlet having a drying agent therein to give access of the ambient atmosphere to the strip or an enclosed body of the composition. In the former mode the degree of color change will depend upon the flow rate, CO concentration and exposure time whereas in the latter mode the degree of color change will be proportional to only the CO concentration and exposure time.

After exposure, the colored material in the indicating composition or strip is extracted with either distilled water or an aqueous buffer solution having a pH of from about 5 to about 12 and preferably from about 8 to about 11. Relatively low cumulative exposures, i.e., up to about 150 ppm-hr, produce yellow aqueous extracts that are more stable than the extracts produced from relatively high exposures, i.e., appreciably greater than about 150 ppm-hr. Either extraction medium is satisfactory for low-exposure determinations, provided that the color depth is measured reasonably soon, i.e., within about 1 hour. Higher exposures lead to more highly colored aqueous extracts which are enhanced considerably in stability by use of aqueous buffered extraction medium. Thus, aqueous buffer solutions are preferred as extraction medium for higher cumulative exposures.

The amount of buffer solution used will vary depending upon factors, such as the pH of the buffer, the indicating composition, the relative amounts of the components in the composition, and the volume of solution needed for colorimetric readout. For a 0.5M pH 10 buffer usually about 10–20 ml of buffer per gram of indicating composition will be used. Preferably, for color stability about 13–18 ml of this buffer are used per gram of indicating composition. One suitable buffer solution is a 0.5M potassium carbonate-potassium borate-potassium hydroxide solution.

Solids are removed from the extract by the use of filtration, centrifuging or any other suitable technique. The depth of color in the extract solution is then measured with a colorimeter and the CO concentration obtained by the use of a set of standards. When the extraction medium is an aqueous buffer solution, the extract solutions are stable for at least 24 hours at room temperature (about 20° C.); hence, colorimetric measurement does not have to be performed immediately.

Still another aspect of the present invention is a CO detector comprising a reaction chamber adapted for exposure of ambient air thereto and containing therein the indicating composition or indicator strip of the invention. The device can have means for drying the ambient air prior to exposure to the reaction chamber or the air can be so dried prior to introduction into the device. The reaction chamber can be a tube with ends capable of being opened to permit passage of ambient air therethrough. A sampling pump can be used to deliver ambient air to the tube at a constant flow rate. Alternatively and preferably, the reaction chamber is a cavity in a blister package which holds in another cavity thereof the extraction medium for the extraction of the colored material and has means whereby said cavities can be placed into fluid communication. The blister-package device can also have diffusion control means to regulate access of the surrounding atmosphere to the reaction chamber. Suitable diffusion control means are described in U.S. Pat. No. 4,208,371, the disclosure of which is incorporated herein by reference.

The best mode contemplated for carrying out the invention is the use of indicator strips as described herein, for cumulative exposures up to about 500 ppm-hr and the use of badges containing the composition of the invention for higher cumulative exposures.

The CO indicating composition and strip of the invention react selectively with CO and not with other common reducing gases. Exposure of the composition to 6,600 ppm of NO in nitrogen, 32,000 ppm of $H_2$ in nitrogen, or 85% by weight formaldehyde gives responses which are only 0–0.68% of those predicted for CO at the same level. Exposure of the composition to 2,600 ppm of ethylene in nitrogen and 6,600 ppm of 1-butene in nitrogen gives responses which are only 8.9% and 9.7%, respectively, of those predicted for CO at the same levels. The highest level which one would expect in the field for these two gases is 2 ppm. At that level, 24 hours' exposure would give "false" CO responses of only 4.3 ppm-hr and 4.7 ppm-hr, respectively. "False" CO responses of this level will ordinarily not be of concern because even normal ambient air contains a few ppm of CO. The composition, indicator strip, device and process of the invention offer the advantage of obtaining a time-stable colored solution which can be measured quantitatively.

The invention is further illustrated by the following examples in which temperatures are in degrees Celsius and percentages are by weight unless otherwise stated.

EXAMPLE 1

Preparation of CO Indicating Composition

Palladium sulfate dihydrate (0.36 g; 0.0015 mole) is dissolved in a solution of 5 g of concentrated sulfuric acid and 25 ml of water. Ammonium molybdate (13.22 g; 0.0107 mole) is dissolved in 100 ml of water at 100°. The resulting palladium solution, which contains some insoluble material, is added to the resulting molybdate solution at 60° to provide a mixture which is allowed to stand at this temperature for 5 minutes. The mixture is filtered through a medium-porosity filter to obtain a clear yellow-brown filtrate which is then added in portions over two minutes to a slurry of 41.1 g of fumed silica, having a surface area of about 400 m$^2$/g, in 500 ml of water. The resulting mixture is shaken for about 5 minutes to effect complete mixing. The bulk of the water in the mixture is evaporated in a rotary evaporator at about 90° and a pressure of 5 mm of Hg to give a yellow powder which is further dried in a vacuum at 95°–100° and a pressure of 0.005$\mu$ for four hours. The product is transferred to a nitrogen-filled chamber, where it is ground in a mortar and sieved in a sieve having 0.420 mm openings (No. 40 U.S. Standard Sieve, 35-mesh for Tyler Standard Screen Scale Sieves). There is obtained 44.7 g of indicating composition as a fine powder that passed through the sieve and 10.0 g of coarser solid that remained behind.

EXAMPLE 2

Measurement of Cumulative CO Exposure

Finely powdered indicating composition prepared in a manner similar to that described in Example 1 (0.30 g) is charged to each of a number of air monitoring badges in an atmosphere of dry nitrogen. Each badge is heat-sealed, placed in a chamber having a CO inlet and exit and means for monitoring the flow (CO screening chamber), and exposed for a measured time to a stream of air containing a known amount of carbon monoxide and passing through the chamber at a measured rate. The CO concentration of the stream is monitored continuously.

At the end of its exposure period each badge is removed from the screening chamber and opened, and 4.0 ml of commercial pH 10.00 buffer solution are added (potassium carbonate-potassium borate-potassium hydroxide 0.5M). The badge is resealed and shaken by hand for two minutes to insure thorough mixing of the buffer solution and the exposed indicating composition. The resulting slurry is transferred to a 20-cc vial and centrifuged for about two minutes, after which supernatant liquid is removed. The depth of color in this liquid is measured in a colorimeter. The observations recorded are summarized in Table 1.

TABLE 1

| CUMULATIVE EXPOSURE RESULTS | | | | | |
|---|---|---|---|---|---|
| CO Concentration (ppm) | Exposure Time (hr) | Indicator Color Before Extraction | Color of Extract | Colorimeter Reading | Reading - 53 |
| 24 | 0 | yellow | yellow | 53* | — |
| " | 1 | " | yellow-green | 70.5* | 17.5 |
| " | 3 | " | light green | 101* | 48 |
| " | 5 | " | light green | 128 | 75 |
| " | 7 | " | light | 151 | 98 |

TABLE 1-continued

CUMULATIVE EXPOSURE RESULTS

| CO Concentration (ppm) | Exposure Time (hr) | Indicator Color Before Extraction | Color of Extract | Colorimeter Reading | Reading - 53 |
|---|---|---|---|---|---|
| 100 | 0 | green-yellow | green yellow | 53 | — |
| " | 0.5 | green-yellow | pale green | 87 | 34 |
| " | 1 | green-yellow | pale green | 120 | 76 |
| " | 1.5 | green-yellow | pale green | 152 | 99 |
| " | 2 | green-yellow | medium green | 193 | 140 |
| " | 3 | green-yellow | medium green | 249 | 196 |
| 272 | 0 | yellow | yellow-green | 53 | — |
| " | 0.17 | " | yellow-green | 77* | 24 |
| " | 0.5 | " | pale green | 137* | 84 |
| " | 1 | yellow-green | green | 211* | 158 |
| " | 1.5 | yellow-green | dark green | 296* | 243 |
| " | 2.0 | yellow | dark green | 363* | 310 |
| 500 | 0 | " | yellow | 53 | — |
| " | 0.5 | yellow-green | dark green | 198 | 145 |
| " | 1 | green-yellow | dark green | 420 | 367 |
| " | 1.5 | green-yellow | dark green | 549 | 496 |
| " | 2 | green-yellow | very dark green | 650 | 597 |
| " | 3 | green-yellow | very dark green | 740 | 687 |
| " | 4.5 | green-yellow | very dark green | 720 | 667 |

*Average of two samples

The results summarized in the foregoing table are depicted graphically in FIG. 1 which shows that a good linear relationship between time of exposure and depth of color exists at each CO concentration.

The depth-of-color stabilities of the extracts obtained in the tests at 24 ppm CO are measured by making colorimeter readings on these solutions 3, 4, 22, and 48 hours after the initial readings. The results are summarized in Table 2 and demonstrate that the extracts are color stable over at least a 24-hour period.

TABLE 2

STABILITY OF COLORIMETER READING

| Exposure Time (hr) | 0 hr (initial) | 3 hr | 4 hr | 22 hr | 48 hr |
|---|---|---|---|---|---|
| 0* | 53 | 54 | 55 | 56 | 61 |
| 1* | 70.5 | 75 | 77 | 78 | 82 |
| 3* | 101 | 106 | 105 | 106 | 112 |
| 5 | 128 | 129 | — | 129 | 137 |
| 7 | 151 | — | — | 151 | 151 |

*Average of two

EXAMPLE 3

A. A sheet about 1 mm in thickness of a composite containing 10% of expanded, amorphous-locked tetrafluoroethylene (TFE) polymer and 90% of fumed silica is cut into strips about 66 mm × 9 mm; and the strips are dried at 300° for 3 hours. The strips are then soaked in concentrated sulfuric acid for 9 days, during which time the acid is replaced with fresh acid five times at about equal intervals by decantation. The strips are then washed with distilled water and dried at a pressure of 40 Pa (0.3 mm of Hg) for 20 hours.

B. A mixture of 0.72 g (0.0030 mole) of $PdSO_4.2H_2O$ and 10.22 g of concentrated sulfuric acid is digested for 5 minutes with gentle agitation to give a brown solution to which distilled water (15 cc) is added carefully. The resulting solution, which contains some finely divided solid, is poured rapidly into a solution of 3.3 g (0.0027 mole) of $(NH_4)_6Mo_6O_{24}.4H_2O$ in 27 cc of water, and the resulting mixture is immediately filtered and stored in glass bottles.

C. A solution is prepared as described in part B, except that 0.36 g (0.0015 mole) of $PdSO_4.2H_2O$ and 5.07 g of concentrated sulfuric acid are used.

D. TFE polymer/silica strips, treated as described in part A, are soaked in the solutions described in parts B and C for 45 minutes, dried in a chemically-resistant glass tray at about 85° to remove excess water, and then dried overnight at a pressure of 40 Pa (0.3 mm of Hg). In the last drying step liquid-nitrogen traps are used to prevent contact of the strips with any oil from the vacuum pump. The resulting indicator strips have a pale yellow color.

E. Indicator strips prepared as described in part D are placed in monitoring badges similar to those described in Example 2 and the devices are placed in a screening chamber similar to that described in Example 2. Air containing 100 ppm of carbon monoxide is passed through the chamber at about 450–500 cc/min. Strips are removed after 15, 30, 60, and 90 minutes. Each strip is removed and extracted by gentle agitation with 6 cc of distilled water for 5 minutes. Colorimetric determinations are made on the extracts at 0, 15, and 30 minutes after the end of a 5-minute extraction period. The results are summarized in the following Table 3.

TABLE 3

| Exposure | | Colorimeter Reading* After | | |
|---|---|---|---|---|
| min | ppm hr | 0 min | 15 min | 30 min |
| Strips treated with solution of part B | | | | |
| 0** | 0 | 8, 11 | 11, 14 | 13, 14 |
| 15 | 25 | 19, 19 | 25, 25.5 | 27, 27 |
| 30 | 50 | 26, 25 | 36, 36 | 47, 35 |
| 60 | 100 | 38, 37 | 63, 63 | 68, 68 |
| 90 | 150 | 53, 65 | 73, 86 | 76, 87 |
| Strips treated with solution of part C | | | | |
| 0** | 0 | 7, 8 | 13, 14.5 | 11, 13 |
| 15 | 25 | 28 | 29 | 29 |
| 30 | 50 | 43 | 46 | 45 |
| 60 | 100 | 76.5 | 81 | 71 |
| 90 | 150 | 92 | 96 | 92 |

*Two readings correspond to duplicate exposures
**Control

Figure 2:
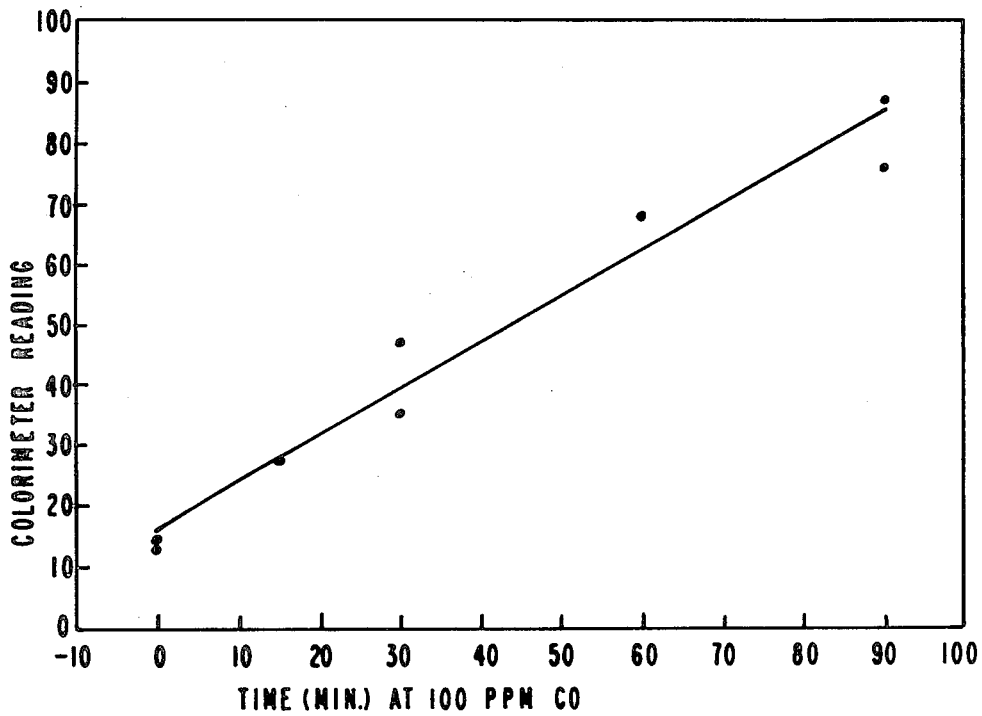
Figure 3:
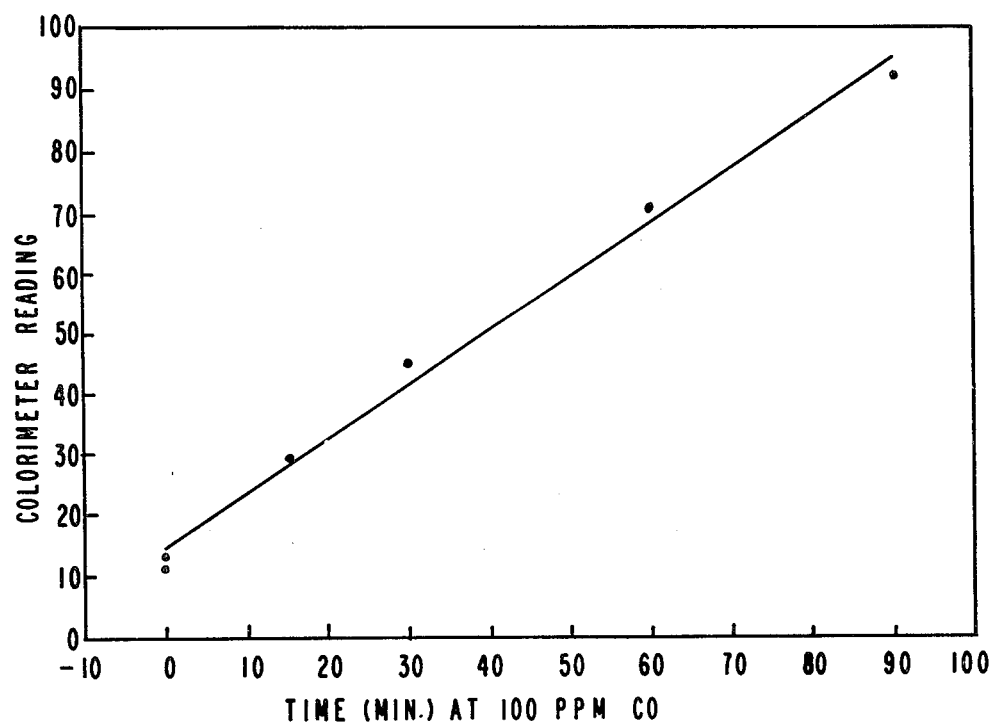

FIGS. 2 and 3 are graphical depictions of the foregoing results and show that a linear relationship exists between time of exposure and depth of color. FIG. 2 represents strips treated with the solution from part B and FIG. 3 represents strips treated with the solution from part C.

We claim:

1. An improved CO indicating composition consisting essentially of silica having dispersed thereon dry residues resulting from the silica having been impregnated with a solution of palladium sulfate, sulfuric acid and ammonium molybdate, the improvement comprising that the silica is fumed silica, said composition (a) having a gram-atom ratio of Mo/Pd of from about 0.1:1 to about 350:1 and a ratio of moles of $SiO_2$/gram atoms of Pd of from about 10:1 to about 5000:1 and (b) being capable of preferentially absorbing CO from ambient air to give a color change and then later being extracted to give an aqueous extract of colored material which is a quantitative measure of ambient CO concentration.

2. The composition of claim 1 wherein the ratio of Mo/Pd is from about 1:1 to about 100:1.

3. The composition of claim 2 wherein the ratio of $SiO_2$/Pd is from about 100:1 to about 1000:1.

4. A process for detecting carbon monoxide comprising exposing ambient air first to a drying agent and then to the indicating composition of claim 1, whereby a color change is effected in said composition proportional to the carbon monoxide content of said air, treating the exposed composition with an extraction medium selected from water and an aqueous buffer solution having a pH of from about 5 to about 12 in order to extract colored material from said composition, separating the resulting extract from the solids of the composition, and measuring color depth in the extract with a colorimeter.

5. The process of claim 4 wherein the extraction medium is water.

6. The process of claim 4 wherein the extraction medium is an aqueous buffer solution having a pH of from about 5 to about 12.

7. The process of claim 6 wherein the aqueous buffer solution has a pH from about 8 to about 11.

8. An improved CO detection device comprising a reaction chamber adapted for exposure of ambient air thereto and containing therein an indicating composition of claim 1, 2 or 3.

9. The detection device of claim 8 comprising in addition an extraction system containing an extraction medium selected from water and an aqueous buffer solution of a pH from about 5 to about 12 and means whereby the extraction system can be placed in fluid communication with the reaction chamber.

* * * * *